United States Patent [19]

Syrett et al.

[11] Patent Number: 5,290,407
[45] Date of Patent: Mar. 1, 1994

[54] SYSTEM FOR CONTROLLING CORROSION IN AN ENVIRONMENT IN WHICH THIN LAYERS OF LOW-PH CORROSIVE FLUIDS ARE FORMED

[75] Inventors: Barry C. Syrett, Palo Alto, Calif.; Gerhardus H. Koch; Neil G. Thompson, both of Columbus, Ohio

[73] Assignee: Electric Power Research Institute, Inc., Palo Alto, Calif.

[21] Appl. No.: 291,567

[22] Filed: Dec. 29, 1988

Related U.S. Application Data

[63] Continuation-in-part of Ser. No. 222,356, Jul. 20, 1988, abandoned, which is a continuation of Ser. No. 863,736, May 16, 1986, abandoned.

[51] Int. Cl.$^5$ ............................................... C23F 13/00
[52] U.S. Cl. ..................................... 204/147; 204/196
[58] Field of Search ................. 204/147, 148, 196, 197

[56] References Cited

U.S. PATENT DOCUMENTS

| | | | |
|---|---|---|---|
| 2,744,863 | 5/1956 | Andrus | 204/197 |
| 2,847,375 | 8/1958 | Murphy | 204/196 |
| 3,216,916 | 11/1965 | Locke | 204/147 |
| 3,841,988 | 10/1974 | Gleason | 204/196 |

OTHER PUBLICATIONS

Ferex 100 Cathodic Protection System, Raychem brochure, Feb. 1986 pp. 1 & 2.
Stratfull, "Knowledge and Needs in the FIeld of of Impressed Current Cathodic Protection: System Control and Monitoring", A paper presented at the FHWA Federally Coordinated Research Program of Highway Research and Developement, Williamsburg, Va. Dec. 1979.
Pennwalt Product Data Sheet CE-226.
Electric Power Research Institute, Inc., "Construction Materials for wet Scrubbers: Update, vol. 1,"Jul. 1984, EPRI CS-3350, pp. 2-8 to 2-88 and pp. 3-94 to 3-96.

*Primary Examiner*—T. Tung
*Attorney, Agent, or Firm*—Heller, Ehrman, White & McAuliffe

[57] ABSTRACT

A system for preventing corrosion of a metallic surface in an environment in which a corrosive condensate with a pH of less than about 3 tends to form on the surface exposed to the environment. The system includes an absorbent lining formed from a concrete material that has a chemical resistance to a low pH and that increases the pH of the environment at the underlying metallic surface. The system further includes a counterelectrode and an electrochemical potential control means connected in electrical circuit with the metallic surface. An electrical potential is maintained upon the metallic surface sufficient to effect cathodic protection.

7 Claims, 2 Drawing Sheets

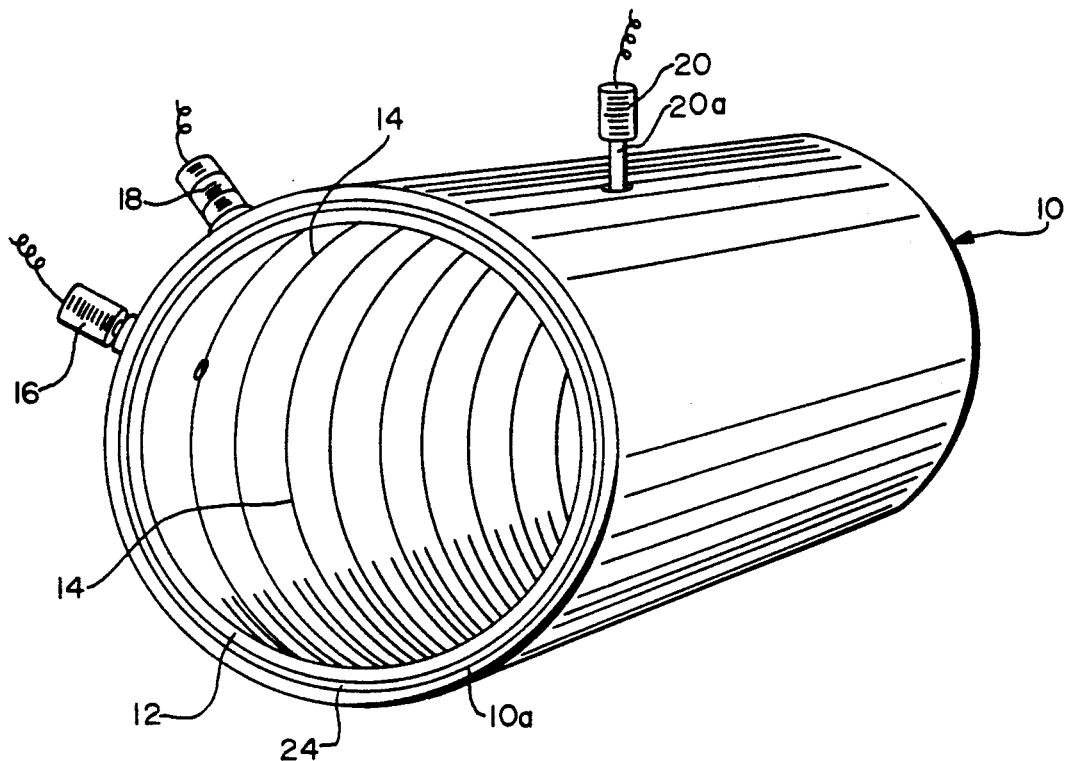
FIG.—1
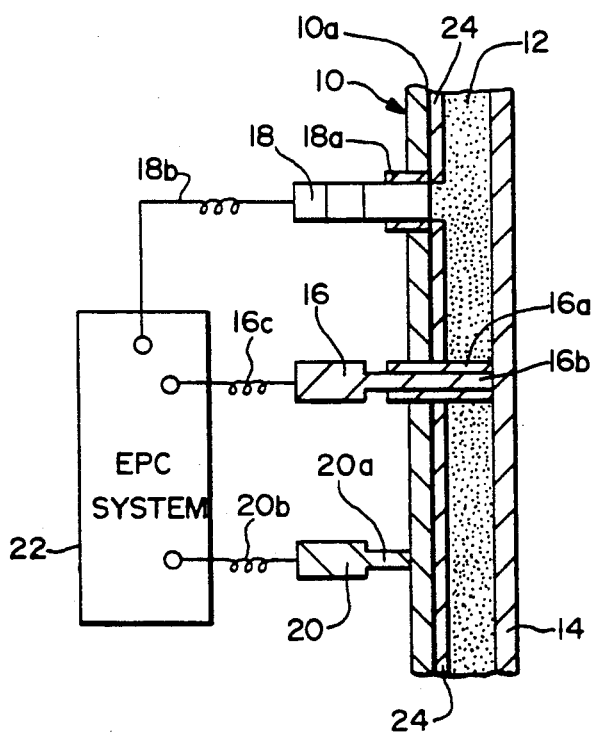
FIG.—2

SYSTEM FOR CONTROLLING CORROSION IN AN ENVIRONMENT IN WHICH THIN LAYERS OF LOW-PH CORROSIVE FLUIDS ARE FORMED

This is a continuation-in-part of patent application Ser. No. 222,356, filed Jul. 20, 1988, now abandoned, which is a continuation of patent application Ser. No. 863,736, filed May 16, 1986, now abandoned.

The present invention relates to the control of corrosion of metallic surfaces exposed to corrosive fluids, and more particularly to a system for controlling corrosion in thin layers of corrosive, acidic fluids.

There are frequent instances where a metallic surface is exposed to a thin layer of a corrosive fluid. For example, the flue gas from a fossil-fueled boiler or combustor contains acidic gases such as sulfur dioxide ($SO_2$), sulfur trioxide ($SO_3$) and oxides of nitrogen ($NO_x$). On its way to the stack, heat is extracted from the flue gas by in-line heat exchangers, such as superheaters, reheaters, and economizers. In addition, heat is lost through the walls of both the ductwork leading to the stack and the stack itself. If the power plant utilizes a flue gas desulfurization (FGD) system, such as a lime or limestone scrubber, additional heat is extracted from the flue gas.

At some point in its journey from the boiler to the top of the stack, the flue gas often cools sufficiently such that its temperature drops below the dewpoint of one or more of the component gases. When this occurs, condensates are deposited on the internal metallic surfaces of the duct or stack. These condensates may contain high levels of halide ions and can be very acidic. In plants without FGD systems, condensates may contain sulfuric acid at concentrations greater than 50% by weight. Even when FGD systems are utilized, it is not uncommon for the pH of condensates in the outlet duct to be less than two.

These condensates are therefore highly corrosive toward materials, such as metals or alloys, used to construct ducts and stacks. A number of systems for preventing or minimizing the corrosion of such metallic surfaces have been considered. Such systems include covering the metallic surfaces with organic or ceramic coatings or linings; using more highly alloyed, more corrosion-resistant alloys; using nonmetallic materials of construction; and reheating the flue gas so that its temperature exceeds the dewpoint. None of these systems, however, have been universally successful and all have certain disadvantages.

The present invention is directed to a system that can be utilized to prevent the corrosion of metallic surfaces by controlling the electrochemical potential of such surfaces. Control of the electrochemical potential of a metal or alloy is a well established approach to controlling corrosion. For instance, cathodic protection of a metallic surface is possible by passing a current from a suitable electrode (counterelectrode) through the corrosive liquid environment to the structure to be protected such that the electrochemical potential of the structure is depressed to a more negative (or less positive) value. Normally, the potential of the cathodically protected surface is within, or close to, the "immune" range of potentials, a range in which the metallic surface is thermodynamically stable in the environment of interest.

Corrosion of metals which experience an active/passive transition may also be controlled in some environments by anodic protection. In cases where the alloy corrodes in the active state at the open circuit potential, a current is passed from a suitable electrode (counterelectrode) to the surface to be protected so that the potential of the surface is increased (to more positive values) from this active potential to a passive potential where a thin, adherent, surface film forms to protect the metal from further corrosion.

In cases where the open-circuit potential of the alloy is within the passive range of potentials but where pitting is a problem, control of the electrochemical potential can again be useful. Here, the metal is cathodically polarized only slightly so that the potential is depressed to the low (most negative) end of the passive range of potentials. In this way, the surface of a metal or alloy is maintained in the passive state while preventing the potential from exceeding the critical pitting potential. Similarly, other forms of corrosion, such as stress corrosion cracking and corrosion fatigue, can often be prevented by controlling the electrochemical potential of the metallic surface.

Corrosion prevention by potential control is a well established technology. For instance, U.S. Pat. No. 3,216,916, issued Nov. 9, 1965, and U.S. Pat. No. 3,409,530, issued Nov. 5, 1968, disclose systems that may be utilized to prevent corrosion by controlling the electrochemical potential of a metallic surface. In the majority of cases, corrosion control by potential control is applied to metals in contact with bulk liquids. For instance, the metal may be immersed in a large body of water (e.g., off-shore platforms immersed in seawater); the metal may surround the corrosive liquid (e.g., a liquid storage tank); or the metal may contact wet soil or other porous, natural materials (e.g., a buried pipeline). In these cases, the counterelectrode(s) can be positioned at some convenient distance from the structure to be protected. The distance is large enough that there is no risk of a counterelectrode coming into direct contact with the structure and, therefore, no risk of creating a short-circuit between the counterelectrode and structure. In the event of a short-circuit, little or no current would flow through the corrosive liquid so the structure would receive little or no protection against corrosion.

The potential control method used in bulk liquids has even been applied successfully in cases where liquid depths of only a few inches are experienced, as described in U.S. Pat. No. 3,216,916, issued Nov. 9, 1965. However, when the metal needing protection is exposed only to thin layers of fluid, say about 1 mm or less in thickness, a different approach must be used so that the short-circuiting of the counterelectrode is avoided. In the case of environments that are of only moderate aggressiveness, such as many aqueous solutions in the pH range of 5 to 9, a method of cathodic protection, described in U.S. Pat. No. 2,744,863, issued May 8, 1956, can be used. Here, the metal structure to be protected is initially coated with an inert, absorbent material, such as felt or asbestos fiber. This coating absorbs the corrosive thin layer of fluid on the metal surface. The counterelectrode is pressed against the absorbent material so that a current can be passed from the counterelectrode through the absorbed liquid to the structure being protected while preventing direct contact (a short-circuit) between the counterelectrode and the structure. A similar approach was described in U.S. Pat. No. 2,847,375, issued Aug. 12, 1956, for protecting steel pilings that are only intermittently wetted by near-neutral seawater.

However, corrosion protection by potential control has never been applied to flue gas ducts, stacks, or similar metallic surfaces where the corrodent not only is a thin fluid film but it is also acidic (pH 3 and below) and very aggressive. The method described in U.S. Pat. No. 2,744,863 (see above), while it would allow for some minimal protection, would not adequately control corrosion in flue gas ducts and stacks. In the acid chloride environments of interest, corrosion rates for carbon steel can be greater than 0.5 inch/year. These rates are one hundred to one thousand times the rates typically experienced in, say, buried steel pipelines and other applications for which conventional cathodic protection is used or in, say, sulfuric acid storage tanks for which conventional anodic protection is used. Correspondingly, the cathodic protection current that would be required to halt the high corrosion rates in the flue gas ducts and stacks would be many orders of magnitude higher than is used in conventional cathodic protection (or anodic protection) systems. It is doubtful that such high currents could be delivered to a duct or stack, partly because commercially available cathodic protection systems would lack the current capacity needed, and partly because current flow would be limited by mass (e.g., hydrogen) transfer away from the protected metal surface. Even if delivery of such high currents was technically feasible, the power costs for such protection would be untenable.

The object of the present invention is to provide a simple and economic system for controlling corrosion of a metallic surface exposed to a thin film of corrosive, acidic fluid.

As may be seen hereinafter, the system disclosed herein is one for preventing corrosion of a metallic surface by a corrosive fluid in an environment in which a corrosive condensate with a pH of less than about 3 tends to form on the surface exposed to the environment. The system includes an absorbent lining capable of absorbing the corrosive condensate and resistant to the corrosive effects of the condensate. The lining is applied to the metallic surface on the side of the surface facing the environment. The lining is formed from a concrete material that has a chemical resistance to a low pH, and chemically changes the environment it contacts; specifically the lining increases the pH of the acidic condensate as it migrates from the lining surface to the lining/metal interface. These characteristics of the concrete material are essential for the cathodic protection of the steel surface to work. The system further includes an electrode that functions as a counterelectrode with respect to the metallic surface. This electrode is spaced from the metallic surface and positioned in contact with the lining. An electrochemical potential control means is connected in electrical circuit between the counterelectrode and the metallic surface to maintain an electrochemical potential upon the metallic surface sufficient to effect cathodic protection of the metallic surface by passing a current from the counterelectrode to the metallic surface through the corrosive condensate absorbed by the absorbent lining.

The present invention differs from a cathodic protection system for rebar in concrete bridge decks and similar structures in two respects. First, the rebar-concrete combination constitutes the material of construction for a bridge deck whereas the material of construction for a flue gas duct or stack is steel, stainless steel, etc.: the absorbent concrete liner in the present invention is an integral part of the corrosion control system and is added only to allow potential control and protection of the structural material. Secondly, the environment experienced by bridge decks and similar structures is generally near-neutral (pH of 5 to 9) and not as corrosive as those experienced by flue gas ducts and stacks; thus, the concrete in a bridge deck need not have the chemical characteristics of the absorbent concrete lining used in the present invention for very corrosive, acid environments.

The system of the present invention will be described in more detail hereinafter in conjunction with the drawings wherein:

FIG. 1 is a schematic view illustrating the present invention utilized in a circular duct;

FIG. 2 is a schematic, sectional view through the duct illustrating a possible arrangement of the system of the present invention.

Figure 3:
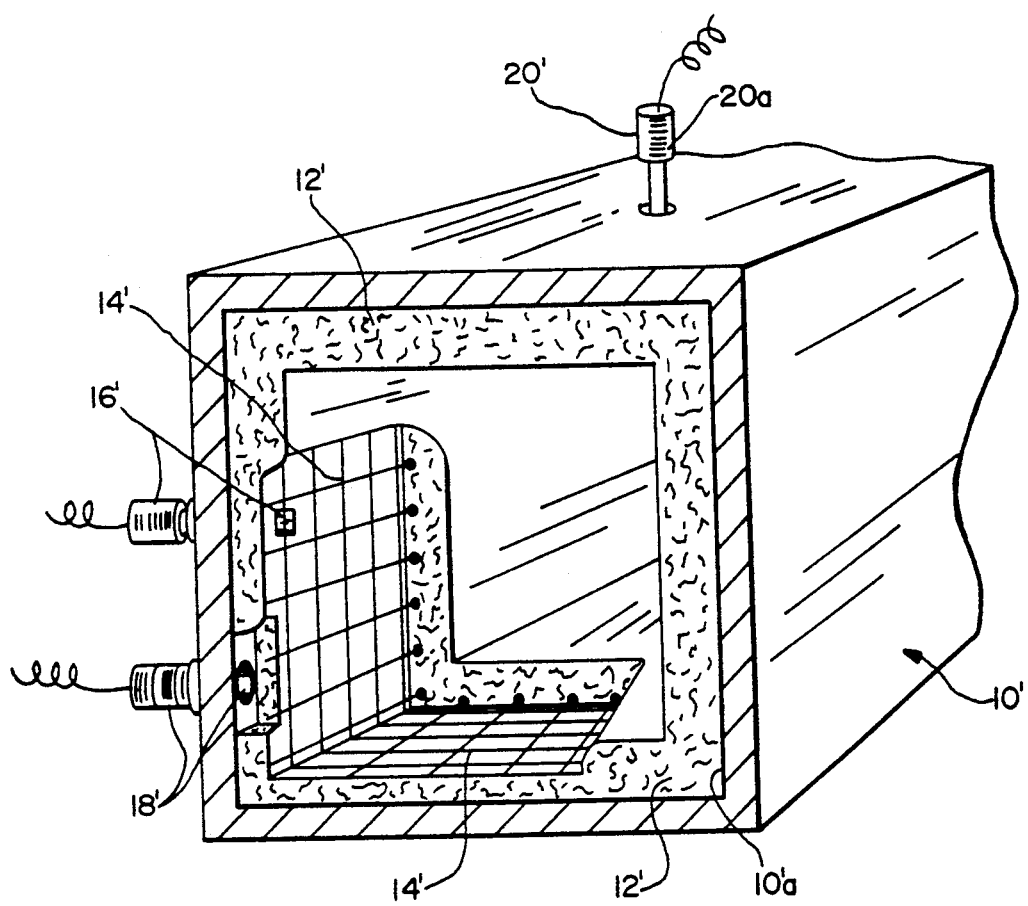
FIG. 3 is a schematic view, partly in section, illustrating the present invention utilized in a rectangular duct.

Referring now to the drawings, attention is directed to FIGS. 1 and 2. These figures illustrate a metallic duct 10 that, in the absence of the system of the present invention, would be exposed to a thin film of corrosive fluid such as a corrosive, acid condensate. The interior metallic surface 10a of the duct thus must be protected from corrosion.

As shown, the duct 10 is lined along its interior surface with an absorbent material 12 so that acid condensates which would otherwise form on the interior surface are absorbed by absorbent lining 12. The lining 12 must be resistant to the environment in which it is utilized. Specifically, it must satisfactorily resist chemical attack by the acid condensates it absorbs. The lining should also not detrimentally interact with the interior surface of duct 10.

The absorbent lining 12 is positioned by any appropriate means, such as by chemical bonding and mechanical fixation devices, in close contact with the interior surface of duct 10 (or, as described later, a non-conductive coating, 24) so that the interior surface is wetted by any condensates absorbed by lining 12. In the outlet duct of a sulfur dioxide scrubber in a fossil-fueled power plant, absorbent lining 12 may be a cementitious material such as Pennwalt Tufchem TM concrete manufactured by the Pennwalt Corporation of Delaware, Ohio. The Pennwalt Tufchem TM concrete is a 100% potassium silicate-bonded concrete free of any hydraulic cements, thus providing resistance to sulfaction-hydration and providing resistance to most acids including sulfuric, hydrochloric, and nitric (product Data Sheet CE-226 (T-12-83) for Tufchem TM).

The concrete increases the pH of the acidic condensate from its initial value, typically pH 1-2, at the concrete surface contacting the flue gas (concrete/flue gas interface) to a value of about 5 at the metal/concrete interface. This increase in pH decreases the aggressiveness of the condensate substantially and makes cathodic protection of the steel feasible. In this regard, the concrete is performing a role that is quite different from the chemically inert absorbent lining used in the cathodic protection system described in U.S. Pat. No. 2,744,863, issued May 8, 1956. In the latter system, the felt or asbestos lining would not increase the pH of an aggressive, acidic condensate and, therefore, corrosion protection would not be feasible.

The system of the present invention further includes a counterelectrode 14 placed in intimate contact with the surface of absorbent lining 12. By way of example, the counterelectrode 14 is shown as a spirally-wound wire or rod. Other geometries, however, are possible and may be more appropriate depending on the particular configuration of the surface to be protected. For instance, a duct may have a square or rectangular cross-section (See FIG. 3), requiring that the counterelectrode be constructed to correspond to such geometries. The counterelectrode could also comprise a conducting fabric.

It may be also necessary to embed counterelectrode 14 into the surface of absorbent lining 12 (See FIG. 3). This would be the case if the temperature gradient through lining 12 is high enough such that the lining is wet near the duct wall 10a but dry at the surface contacting the gas or other corrosive fluid passing through the duct. Embedding counterelectrode 14 into the absorbent lining 12 may also be a convenient method of providing structural support to the counterelectrode.

At intervals along the length of the duct, the duct is penetrated to make external connections to counterelectrode 14. Such connections, indicated generally by reference numeral 16, are electrically-isolated from the duct wall and lining 12. The electrical connection 16 may comprise a tubular sleeve 16a through which is extended an electrically-conductive stud or bolt 16b. The tubular sleeve 16a extends through the duct wall and the absorbent lining. Sleeve 16a is fabricated from an electrically-insulating material such as Teflon manufactured by E.I. DuPont de Nemours Co. The electrically-conductive member 16b is appropriately positioned in sleeve 16a to be in contact with counterelectrode 14 so that a conductive path is formed therebetween. The electrical connection 16 further includes an electrical lead 16c that connects the counterelectrode 14 in an electrical circuit with the electrical potential control ("EPC") system 22. The electrical lead 16c may extend through a suitable conduit (not illustrated). If appropriate, electrical connection 16 may be enclosed within a weathertight or gas-tight housing (also not illustrated).

The system of the present invention may also include a reference electrode 18. Reference electrode 18 may be positioned at, or close to, the interface between lining 12 and the interior surface 10a of duct 10. The reference electrode is connected in circuit with the EPC system 22, and is electrically isolated from duct 10. To this end, reference electrode 18 may extend through a tubular, electrically-insulating sleeve 18a to be in electrolytic contact with lining 12. An electrical lead 18b is provided to connect the reference electrode to EPC system 22. The electrical lead 18b may extend through an appropriate conduit and that portion of reference electrode 18 exterior to duct 10, may be enclosed, if desired, within a weathertight or gas-tight housing. Neither the housing nor the conduit are illustrated.

The duct 10 is connected in electrical circuit with EPC system 22 by means of duct electrical connection 20. Connection 20 may comprise an electrically-conductive stud or member 20a disposed in electrically-conducting contact with the exterior wall of duct 10. An appropriate electrical lead 20b connects member 20a, and thus duct 10, in circuit with EPC system 22.

The specific construction of the counterelectrode connection 16, the reference electrode 18 and the duct connection 20 would be readily apparent and well known to those of ordinary skill in the art, and hence the construction of these components are not illustrated nor described in any greater detail.

The EPC system 22 is capable of controlling the electrochemical potential of the duct wall surface. For instance, if cathodic polarization is required, EPC system 22 would comprise a conventional cathodic protection system. However, as discussed heretofore, a cathodic protection system is just one possible electrochemical potential control system that may be utilized within the context of the present invention.

An essential feature of EPC system 22 is that it is capable of passing current between the counterelectrode 14 and the duct wall (via duct connection 20) through the corrosive, acidic fluid absorbed in absorbent lining 12, thereby providing control of the electrochemical potential of the duct wall to prevent corrosion.

If reference electrode 18 is incorporated into the system, more precise control, as is well known in the art, of the electrochemical potential of the metallic surface of duct 10 is possible. The EPC system 22 measures the potential difference between the reference electrode and the duct surface, comparing that difference to a predetermined value. If the potential difference does not correspond to the predetermined or preset value, then the system automatically increases or decreases the current, as necessary, from counterelectrode 14 through the corrosive fluid in absorbent lining 12 to the surface of duct 10, until the measured potential difference between the reference electrode and the duct surface is equal to the preset value, i.e. the desired value for corrosion control.

The system of the present invention may be installed in stacks, ducts, or in any other areas that are exposed to corrosive condensates continuously or only intermittently. If absorbent lining 12 is dry, little or no current will flow from counterelectrode 14 to the duct wall, because the dry lining is either poorly conducting or non-conducting. However, under such conditions, corrosion protection is not required, since corrosion rates are negligibly low if the duct wall is dry.

The absorbent lining allows currents to be passed from the counterelectrode to the metallic surface requiring protection from corrosion. Without absorbent lining 12, it would be quite impractical, if not impossible, to pass such currents. The absorbent lining facilitates the required intimate contact between the counterelectrode and the corrosive fluid, while also eliminating the possibility of an electrical short-circuit between the counterelectrode and the metal surface being protected.

The system of the present invention may also include a non-conductive or poorly conducting coating 24 disposed between the interior wall of duct 10 and absorbent lining 12. The coating 24 is, however, not located at those locations along the duct where counterelectrode connections 16 or reference electrode connections 18 exist. This is necessary in order to provide the appropriate electrolytic and electrical circuit path for operation of the system. Coating 24 is a corrosion-resistant coating, but is subjected to lower temperatures and may experience a less corrosive environment than lining 12. Thus, coating 24 may be constructed from a broader range of materials. For example, it may be fabricated from a material such as an epoxy, that might not be resistant to direct attack by the duct environment. Coating 24 may provide additional protection to duct 10. It also may provide a more economical system as less current and power would be utilized, since current only passes from counterelectrode 14 to the interior surface of duct 10 at those points where there is a break (a "holiday") in the coating 24. Holidays can be small (e.g. pinholes created during application of the coating) or large (e.g. caused by mechanical damage) but they are usually present. Thus, in the absence of the EPC system, the coating 24 and absorbent lining 12 alone cannot offer complete protection from corrosion.

FIG. 3 illustrates the present invention utilized in a rectangular duct 10' with counterelectrode 14' embedded in absorbent layer 12'. Counterelectrode 14' has a square-mesh geometry, and as discussed, electrical connection 16' is provided to make external connections to counterelectrode 14'. Reference electrode 18' is in electrolytic contact with lining 12', and electrical connection 20' connects duct 10' in electrical circuit with the EPC system.

The system of the present invention may be utilized in the outlet ducts and stacks of power plants. Additionally, the system may be utilized in various other situations where metallic surfaces are susceptible to corrosion by a thin surface layer of corrosive, acidic fluid. Such situations include those where the temperature of a gaseous environment drops below the dewpoint so that acidic condensates form on the metallic surface to be protected. The system may also be utilized in splash zones often found at the junction between a liquid phase and a gas or vapor phase. For instance, the system of the present invention may be applied at the inlet of a sulfur dioxide scrubber where the limestone slurry may splash from the quench section into the inlet duct and cause severe corrosion.

Although certain specific embodiments of the invention have been described herein in detail, the invention is not to be limited only to such embodiments, but rather only by the appended claims.

What is claimed is:

1. A method for cathodic protection of a metallic surface comprising:
   applying to the side of the metallic surface facing a flue gas and on which a corrosive condensate with a pH of less than about 3 would occur on the metallic surface in the absence of the method, a layer of an acid resistant concrete that has a chemical resistance to a low pH and that chemically affects the corrosive condensate by increasing its pH to a value where cathodic protection is feasible;
   absorbing the corrosive condensate in said layer of acid resistant concrete; and
   inducing an electrochemical potential between said metallic surface and the absorbed condensate in said layer sufficient to effect cathodic protection of the metallic surface.

2. The method of claim 1 in which, in the step of inducing an electrochemical potential, the electrochemical potential induced is maintained at a predetermined value controlled by a reference electrode.

3. The method of claim 1 or 2 in which the metallic surface is part of a flue gas duct or stack and in which the step of applying is a step of applying to the interior facing surface of the duct or stack.

4. An apparatus for preventing corrosion of a metallic surface exposed to a flue gas, comprising:
   an acid-resistant concrete disposed on the metallic surface and exposed to the flue gas wherein a thin layer of corrosive condensate with a pH of less than about 3 tends to form on said concrete, said concrete forming a lining capable of absorbing the corrosive condensate and having a chemical resistance to a low pH, and chemically affecting the corrosive condensate by increasing its pH before it reaches the metallic surface to a value where cathodic protection is feasible;
   a counterelectrode in contact with said concrete and spaced from said metallic surface; and
   electrochemical potential control means connected in an electrical circuit between said couterelectrode and said metallic surface for maintaining an electric potential upon said metallic surface sufficient to effect cathodic protection of said metallic surface by passing a current from said counterelectrode to said metallic surface through the corrosive condensate absorbed by said lining.

5. The apparatus of claim 4 further including an electrically non-conductive, corrosion-resistant coating disposed between said metallic surface and said lining which coating has breaks that permit the passage of a current therethrough.

6. An apparatus in accordance with claim 4 for preventing corrosion of a metallic surface by a corrosive condensate further including:
   a reference electrode in electrolytic contact with said lining and electrically-isolated from said metallic surface and from said counterelectrode except through the corrosive condensate in said lining; and
   said electrochemical potential control means connected in electrical circuit with said counterelectrode, said reference electrode and said metallic surface for maintaining the potential of said metallic surface at a predetermined cathodic protection value with respect to said reference electrode.

7. The apparatus of claims 4, 5, or 6 in which the metallic surface is an interior facing surface of metal forming a flue gas duct or stack.

* * * * *